Aug 7, 1951 H. C. SWIM Plant Pat. 1,028
ROSE PLANT
Filed March 31, 1950
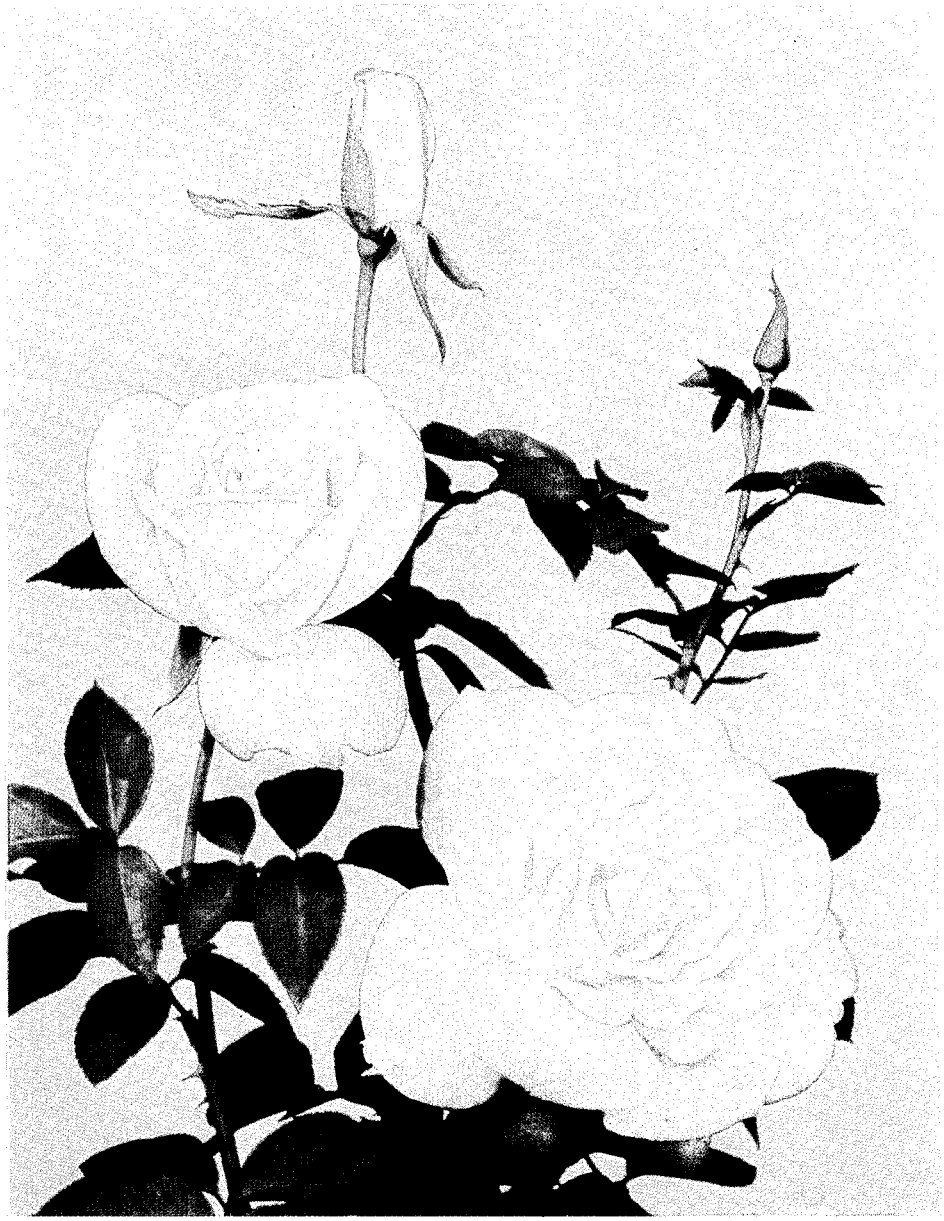
Inventor.
H. C. Swim
By: Robb & Robb
attorneys.

Patented Aug. 7, 1951

Plant Pat. 1,028

UNITED STATES PATENT OFFICE 1,028

ROSE PLANT

Herbert C. Swim, Ontario, Calif., assignor to Armstrong Nurseries, Inc., Ontario, Calif., a corporation of California Application March 31, 1950, Serial No. 153,161

1 Claim. (Cl. 47—61)

The present invention relates to a new and distinct variety of rose plant of the hybrid tea class, originated by crossing the variety "Charlotte Armstrong" (Plant Pat. No. 455) with the variety "Glowing Sunset" (Plant Pat. No. 104).

The breeding above referred to has resulted in a variety which is not only widely different from its parents, but also different from any other hybrid tea rose variety of which I am aware. The unique combination of dominant distinctions are briefly summarized as follows:

(1) The plants of the new variety are characterized by a vigorous habit of growth, with large, leathery, non-glossy foliage;

(2) The buds of the new variety are large in size and long-pointed to urn-shaped, and open to flowers with high centers at first, later becoming flat and open;

(3) Both buds and open flowers are of colors ranging in the pastel shades as hereinafter more fully described and illustrated in the accompanying drawing; and (4) The flowers are produced on normal-strength but long stems.

This new variety of rose differs from both of its parents in the combination of its characteristics, although it resembles one or the other parent in several individual respects. While the new variety has a much longer bud than its pollen parent "Glowing Sunset," the color is distinctly different in that the new variety is near Begonia or Porcelain Rose, whereas the color of "Glowing Sunset" is popularly described as orange. The plants of the new variety are more vigorous than those of "Glowing Sunset" and their foliage is non-glossy, while the foliage of this parent is glossy.

In comparison with the seed parent "Charlotte Armstrong," the color of the buds and open flowers of the parent variety is popularly described as red to cerise, as distinguished from the color of the new variety as above referred to. Moreover, the new variety has fewer prickles than "Charlotte Armstrong."

Asexual reproduction of the new variety by budding at Ontario, California, shows that the foregoing characteristics come true to form and are established and transmitted through succeeding propagations.

In the drawing are shown specimens of the new variety, depicting as nearly as possible the various distinctions and novel characteristics referred to above, the blooms being illustrated in their different stages from small bud to full-open flower.

The following is a detailed description of the new variety, with color terminology in accordance with Robert F. Wilson's Horticultural Color Chart (1941) and Ridgway's Color Standards and Color Nomenclature (1912):

Type: Tall; bush; outdoor; seedling; for cut flowers and garden decoration.

Class: Hybrid tea.

Breeding: Seedling.

*Seed parent.*—"Charlotte Armstrong."

*Pollen parent.*—"Glowing Sunset."

*Flower*

Locality where grown: Ontario, California.

Flowers Borne: Usually singly to stem; on normal strength but long stems.

Quantity of bloom: Abundant; outdoors.

Continuity: Continuous during growing season.

Fragrance: Moderate; tea.

Bud:

*Peduncle.*—Average length to long; average caliper; bending to erect; numerous gland-tipped cilia and few prickles. Color—Lettuce Green, Plate V (Ridgway), tinged very lightly with Acajou Red, Plate XIII (Ridgway).

*Before calyx breaks.* — Size — medium. Form—Long pointed to ovoid with a conspicuous neck; with foliaceous appendages, gland-tipped cilia and glandular bloom on the surface of the bud; usually with foliaceous parts extending beyond the tip of the bud equal to one-fourth or more of its length.

*As calyx breaks.*—Color—Delft Rose, Plate o20/1, page 108 (Wilson).

*Sepals.*—Inner surface with fine, woolly tomentum. Margins not covered by adjacent sepals have stipitate glands. A sepal has either both margins covered or both uncovered except for the fifth or odd sepal. Margins without glands have woolly tomentum. Glandular margins have several small foliaceous appendages.

*As first petal opens.*—Size—average to large. Form—medium length to long; urn-shaped. Color—outside—base of Canary Yellow, Plate 2/2, page 2 (Wilson), shading into Chinese Yellow, Plate 606/2, page 68 (Wilson), near base. Toward margins and distal part of petal, color becomes between Begonia, Plate 619/1, and Begonia, Plate 619/2, page 146, (Wilson). Inside—base of Canary Yellow, Plate 2/2, page 2 (Wilson), with rest of petal near Porcelain Rose, Plate 620, page 147 (Wilson).

*Opening.*—Opens up well; is not retarded from opening by hot or dry weather.

Bloom:

*Size when fully open.*—Large; 5 inches to 6 inches.

*Petalage.*—Double; from 20 to 25 petals, plus 0 to 6 petaloids, arranged regularly.

*Form.*—Very high-centered at first; later becoming very flat and open when in upright position; petals remaining at first somewhat cupped with tips reflexed outward; becoming later at maturity, loosely cupped with tips reflexed outward.

Petals:

*Texture.*—Medium thick; with inside slightly satiny and outside slightly shiny.

*Shape.*—Outside—broadly obovate with apex flat; sometimes with 1 to 3 notches. Intermediate—obovate with apex flat. Inside—obovate with apex flat.

*Colors.*—Colors may be modified by being shaded or tinted with other colors.

This description of a newly opened flower was made from a rose grown outdoors in the month of August, 1949, at Ontario, California:

*Color.*—*Outside petal*—outside surface: Canary Yellow, Plate 2/2, page 2 (Wilson), base (point of attachment) with rest of petal near Chinese Yellow, Plate 606/3, page 68 (Wilson), shaded near margins with Porcelain Rose, Plate 620/3, page 147 (Wilson); inside surface: Canary Yellow, Plate 2/2, page 2 (Wilson), base with rest of petal between shades of Porcelain Rose, Plate 620/2, page 147, and Porcelain Rose, Plate 620/3, page 147 (Wilson), sometimes shading into Begonia, Plate 619/2, page 146, or Begonia, Plate 619/3, page 146 (Wilson). *Intermediate petal*—outside surface: Canary Yellow, Plate 2/2, page 2 (Wilson), base with the rest of the petal Chinese Yellow, Plate 606/2, page 68 (Wilson), shaded near margins with Porcelain Rose, Plate 620/2, page 147 (Wilson); inside surface: Canary Yellow, Plate 2/2, page 2 (Wilson), base with rest of petal between Porcelain Rose, Plate 620/2, page 147 (Wilson), and Begonia, Plate 619/2, page 146 (Wilson). *Inner petal*—outside surface: Canary Yellow, Plate 2/2, page 2 (Wilson), base shading into Chinese Yellow, Plate 606/2, page 68 (Wilson), with rest of petal near margins between Porcelain Rose, Plate 620/1, page 147 (Wilson), and Begonia, Plate 619/1, page 146 (Wilson); inside surface: Canary Yellow, Plate 2/2, page 2 (Wilson), base with rest of petal between Porcelain Rose, Plate 620/1, page 147 (Wilson), and Begonia, Plate 619/1, page 146 (Wilson), sometimes shaded with Porcelain Rose, Plate 620, page 147 (Wilson).

This description was made from a rose that was open for three days outdoors in the month of August, 1949, at Ontario, California:

*Color.*—*Outside petal*—outside surface: near white tinged with Porcelain Rose, Plate 620/3, page 147 (Wilson). At base near Canary Yellow, Plate 2/2, page 2 (Wilson); inside surface: near white tinged with Porcelain Rose, Plate 620/3, page 147 (Wilson). At base near Canary Yellow, Plate 2/2, page 2 (Wilson). *Inside petal*—outside surface: near white tinged with Porcelain Rose, Plate 620/3, page 147 (Wilson). At base near Canary Yellow, Plate 2/2, page 2 (Wilson); inside surface: near white tinged with Porcelain Rose, Plate 620/3, page 147 (Wilson). At base near Canary Yellow, Plate 2/2, page 2 (Wilson).

*General color effect.*—Newly opened flower—near Begonia, Plate 619/1, page 146 (Wilson). The outer petals are somewhat lighter, approaching white. Three days open—near white tinged with Porcelain Rose, Plate 620/3, page 147 (Wilson).

*Behavior.*—Drop off cleanly; not particularly affected by cold, hot, wet or dry weather, except minor changes in flower color.

*Flower longevity.*—On bush in garden—3 days in August. Cut roses grown outdoors kept at living room temperatures—3 days in August.

*Reproductive organs*

Stamens: Many; arranged regularly about pistils.

Filaments: Medium length; few without anthers. Color—Lemon Yellow, Plate 4/1, page 4 (Wilson).

Anthers: Medium size to large; all open at once approximately. Color—along margins color is near Saffron Yellow, Plate 7/2, page 7 (Wilson). Other areas are Canary Yellow, Plate 2/3, page 2 (Wilson).

Pollen: Moderately abundant. Color—Saffron Yellow, Plate 7/2, page 7 (Wilson).

Pistils: Average number to many; approximately 65 in number.

Styles: Moderately uneven; average length; average caliper; somewhat loosely bunched.

Stigma: Color—near Mimosa Yellow, Plate 602/3, page 143 (Wilson). Style color near Cardinal Red, Plate 822/3, page 168 (Wilson).

Ovaries: Most protruding from calyx.

Hips: Large; turbinate to globular; walls thick.

Sepals: Permanent; long; reflexed. Color—inside: Courge Green, Plate XVII (Ridgway) tinted with Acajou Red, Plate XIII (Ridgway) modified by heavy white tomentum; outside: near Courge Green, Plate XVII (Ridgway).

Seeds: Average number to many; medium size; 10 to 50 in number.

*Plant*

Foliage:

*Leaves.*—Compound of usually 5 to 7 leaflets; normal number; medium to large; moderately heavy to leathery; non-glossy.

*Leaflets.* — Shape — Ovate-lanceolate with apex acute; base obtuse; margin serrate.

*Color.*—*Mature*—upper surface—near Parsley Green, Plate 00962, page 193 (Wilson); under surface—near Asphodel Green, Plate XLI (Ridgway). *Young*—upper surface—near Lettuce Green, Plate V (Ridgway) with margins heavily shaded with Erythrite Red, Plate 0027/1, page 190 (Wilson); under surface—near Erythrite Red, Plate 0027/2, page 190 (Wilson), with some Lettuce Green, Plate V (Ridgway), showing through.

*Rachis.*—Average caliper. Upper side—grooved with some stipitate glands on edges; under side—moderately prickly.

*Stipules.*—Long; adnate with long points turning out at an angle of 45°.

*Disease.*—More than average resistance to mildew.

Growth:

*Habit.*—Upright; spreading; branching average.

*Growth.*—Very vigorous.

*Canes.*—Medium caliper to heavy.

*Main stems.*—Color—near Asphodel Green, Plate XLI (Ridgway). Older canes streaked with Cinnamon, Plate XXIX (Ridgway). Large prickles—several to many; hooked slightly downward; with medium length, moderately broad base. Color—varies between Cinnamon-Buff, Plate XXIX (Ridgway), to Russet, Plate XV (Ridgway). Small prickles and hairs—none.

*Branches.*—Color — near Asphodel Green, Plate XLI (Ridgway). Large prickles—several to many; long; hooked slightly downward; with medium length moderately broad base. Color—near Tawny, Plate XV (Ridgway). Small prickles and hairs—none.

*New shoots.*—Color—near Cosse Green, Plate V (Ridgway), shaded with Pompian Red, Plate XIII (Ridgway). Large prickles—few; hooked slightly downward; with moderately short narrow base. Color—Light Dull Green-Yellow, Plate XVII (Ridgway) shaded at base with Acajou Red, Plate XIII (Ridgway). Small prickles and hairs—none.

I claim:

A new and distinct variety of rose plant of the hybrid tea class, characterized as to novelty by the vigorous habit of growth of the plant, by its large, leathery, non-glossy foliage, by its large, long-pointed to urn-shaped buds opening to flowers with high centers at first and later becoming flat and open, by the production of its flowers on normal-strength but long stems, and by the color ranging in the pastel shades in both buds and open flowers, substantially as shown and described.

HERBERT C. SWIM.

No references cited.